(12) United States Patent
Sullivan

(10) Patent No.: US 12,121,736 B2
(45) Date of Patent: *Oct. 22, 2024

(54) WCD WITH PACING ANALGESIA

(71) Applicant: WEST AFFUM HOLDINGS DAC, Dublin (IE)

(72) Inventor: Joseph L. Sullivan, Kirkland, WA (US)

(73) Assignee: WEST AFFUM HOLDINGS DAC, Dublin (IE)

(*) Notice: Subject to any disclaimer, the term of this patent is extended or adjusted under 35 U.S.C. 154(b) by 117 days.

This patent is subject to a terminal disclaimer.

(21) Appl. No.: 17/221,693

(22) Filed: Apr. 2, 2021

(65) Prior Publication Data
US 2021/0220658 A1    Jul. 22, 2021

Related U.S. Application Data

(63) Continuation of application No. 15/887,785, filed on Feb. 2, 2018, now Pat. No. 10,967,193.
(Continued)

(51) Int. Cl.
*A61N 1/00* (2006.01)
*A61N 1/04* (2006.01)
*A61N 1/39* (2006.01)

(52) U.S. Cl.
CPC ......... *A61N 1/3904* (2017.08); *A61N 1/0412* (2013.01); *A61N 1/046* (2013.01); *A61N 1/3993* (2013.01); *A61N 1/3987* (2013.01)

(58) Field of Classification Search
CPC ...... A61N 1/3904; A61N 1/0428–0456; A61N 1/0412; A61N 1/3993; A61N 1/046; A61N 1/3987
See application file for complete search history.

(56) References Cited

U.S. PATENT DOCUMENTS 3,724,355 A    4/1973  Busch et al.
4,583,524 A    4/1986  Hutchins
(Continued)

FOREIGN PATENT DOCUMENTS

DE    2005060985 A2    6/2007
EP       2305110 A1    4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Scott M. Getzow
(74) *Attorney, Agent, or Firm* — Polsinelli PC

(57) ABSTRACT

An external defibrillator system such as a WCD is also capable of providing transthoracic pacing and drug delivery (e.g., pain-reducing drugs and/or a sedatives) to a patient. The drug(s) may be included in the therapy electrode electrolyte and dispensed for defibrillation, cardioversion and/or pacing therapy. Alternatively, the drug(s) may be stored in a separate reservoir and dispensed during pacing therapy. The drug(s) may be dispensed to a patient after a successful defibrillation therapy. The pacing therapy may be delivered a set time-period after the drug(s) were dispensed. A relatively small electric current may be delivered to the area of the patient on which the drug(s) were dispensed to facilitate drug absorption.

20 Claims, 7 Drawing Sheets

REVLEVANT COMPONENTS OF EXTERNAL
DEFIBRILLATOR WITH PACING ANALGESIC MODULE

Related U.S. Application Data

(60) Provisional application No. 62/454,661, filed on Feb. 3, 2017.

(56) References Cited

U.S. PATENT DOCUMENTS

| | | |
|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A * | 1/1992 | Heilman ............... A61N 1/046 607/142 |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 5,954,753 A * | 9/1999 | Alt ....................... A61N 1/3704 607/8 |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,037,271 B2 * | 5/2015 | Kaib .................. A61M 35/003 607/153 |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2007/0150008 A1 * | 6/2007 | Jones .................. A61N 1/0492 604/20 |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0100622 A1 * | 4/2014 | Sullivan ............... A61N 1/3962 607/4 |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0135706 A1 * | 5/2016 | Sullivan ............... A61B 5/4803 600/509 |
| 2016/0253471 A1 * | 9/2016 | Volpe .................. G06F 11/1417 607/5 |
| 2016/0256104 A1 | 9/2016 | Romem et al. |

(56) References Cited

U.S. PATENT DOCUMENTS

| | | | |
|---|---|---|---|
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0143977 A1 | 5/2017 | Kaib et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0160304 A1* | 5/2019 | Ibrahim ............... | A61N 5/0622 |
| 2019/0321650 A1 | 10/2019 | Raymond et al. | |

FOREIGN PATENT DOCUMENTS

| | | | |
|---|---|---|---|
| JP | 4320257 A | 3/2005 | |
| JP | 5963767 A | 1/2014 | |
| JP | 2014526282 A | 10/2014 | |
| WO | 98/39061 A2 | 9/1998 | |
| WO | 1998039061 A2 | 9/1998 | |
| WO | 2011/146448 A1 | 11/2011 | |
| WO | 2012/064604 A1 | 5/2012 | |
| WO | 2012/151160 A1 | 11/2012 | |
| WO | 2015/056262 A1 | 4/2015 | |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

Klein, H. U., Goldenberg I., & Moss, A. J., Risk Stratification for Implantable Cardioverter Defibrillalor Therapy: The Role of the Wearable Cardioverter-Defibrillalor, Clinical update, European Heart Journal, May 31, 2013, pp. 1-14, doi:10.1093/eurheartj/eht167, European Society of Cardiology.

Heartstart MRx and XL AED Algorithm—Application Nole, Jul. 2001, Edition 2 Philips Healthcare, USA.

The LifeVest Network/Patient Data Management System, Zoll, 2015, 20C0503 Rev A.

* cited by examiner

FIG. 2 SAMPLE COMPONENTS OF EXTERNAL DEFIBRILLATOR

REVLEVANT COMPONENTS OF EXTERNAL DEFIBRILLATOR WITH PACING ANALGESIC MODULE

WCD WITH PACING ANALGESIA

CROSS REFERENCE TO RELATED PATENT APPLICATIONS

This patent application is a continuation of U.S. patent application Ser. No. 15/887,785, filed on Feb. 2, 2018, which claims benefit of U.S. Provisional Patent Application Ser. No. 62/454,661, filed on Feb. 3, 2017, and is hereby incorporated by reference in its entirety.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

WCDs currently available to the public can provide therapy for VT/VF but not brady/asystolic arrest. Transvenous pacing implemented in implanted pacing devices is painless, but transthoracic pacing is generally not tolerated by conscious patients. EMS caregivers will typically sedate a patient before initiating transthoracic pacing in the field. Asystole is a significant cause of death in the WCD population. It is believed that prior art WCDs are not implemented to treat asystole patients because if the treatment was effective and an asystole patient regained consciousness, the patient would immediately press the divert button or remove the vest to stop the pain from the transthoracic pacing therapy.

All subject matter discussed in this Background section of this document is not necessarily prior art, and is not to be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor. This approach in and of itself may also be inventive.

BRIEF SUMMARY

The present description describes instances of wearable cardioverter defibrillator (WCD) systems, storage media that store programs, and methods.

According to some aspects, a WCD system includes electrodes with which it senses an ECG signal of the patient. In addition, in some aspects the WCD also has a transthoracic pacing capability and the ability to deliver a pain-reducing drug to the patient. In some aspects, a pain-reducing drug is included in the therapy electrode electrolyte. In some aspects, this electrolyte with pain-reducing drug is released onto the patient's skin prior to a therapy, which can be pacing, cardioversion and/or defibrillation.

According to some aspects, the pain-reducing drug is stored in a separate container and dispensed during pacing therapy. In some aspects, the pain-reducing drug is dispensed to a patient after a successful defibrillation therapy. In some aspects, the pain-reducing drug is release prior to the electrolyte, with the electrolyte being released after a delay so that the pain-reducing drug to take effect before the pacing therapy is provided.

According to some aspects, in addition to or instead of a pain-reducing drug, a sedative is dispensed to the patient prior to providing defibrillation and/or pacing therapy.

According to some aspects, an electrical current is provided in the area at which the drug is dispensed on the patient's skin to facilitate absorption of the drug.

One or more features of the above summarized aspects may be omitted from or combined, according to various embodiments. An advantage that can be provided by disclosed aspects is that a conscious patient may be able to tolerate pacing therapy provided by the WCD.

DETAILED DESCRIPTION

As has been mentioned, the present description is about wearable cardioverter defibrillator (WCD) systems, and related storage media, programs and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
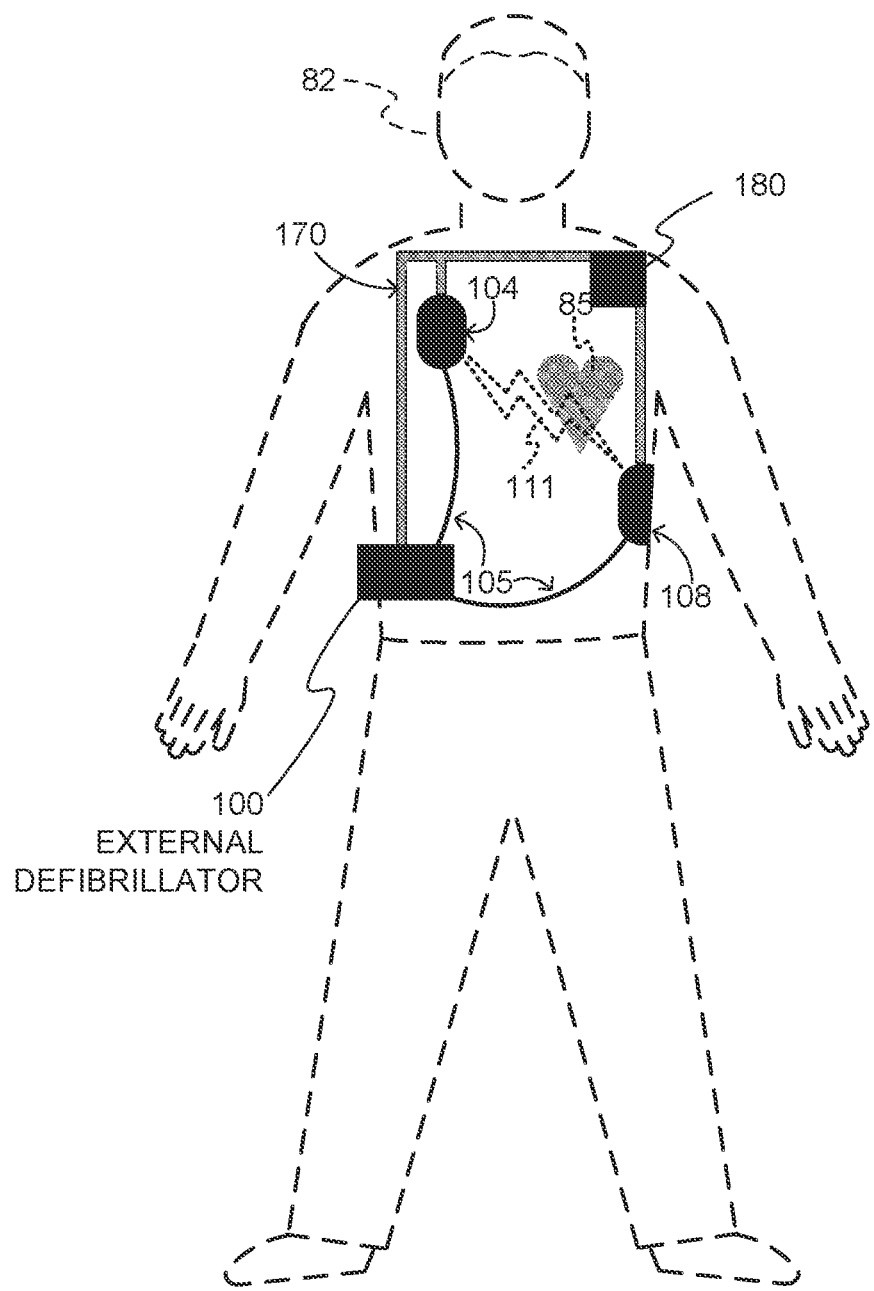
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data (also referred to herein as patient parameter signals) can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
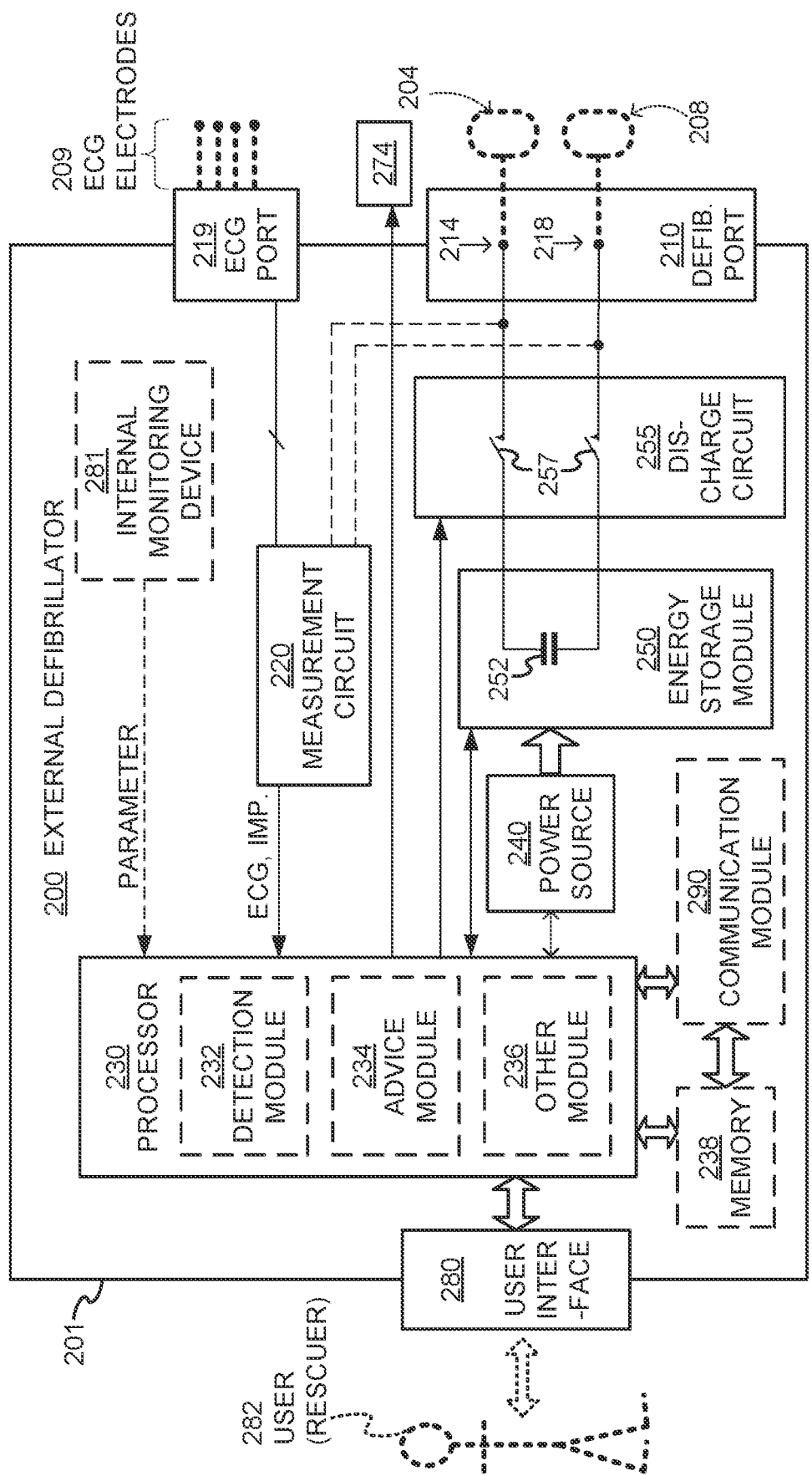
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals (also referred to herein as patient parameter signals). Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal from a processor 230, which is described more fully later in this document.

Defibrillator 200 in embodiments also includes a measurement circuit 220, as one or more of its sensors or transducers. Measurement circuit 220 senses one or more electrical physiological signals of the patient from sensor port 219, if provided. Even in embodiments of defibrillator 200 that lack sensor port 219, measurement circuit 220 may selectively obtain physiological signals through nodes 214, 218 instead, when defibrillation electrodes 204, 208 are attached to the patient. In these embodiments, the physiological input reflects an ECG measurement. The patient parameter can be an ECG, which can be sensed as a voltage difference between electrodes 204, 208. In addition, the patient parameter can be an impedance, which can be sensed between electrodes 204, 208 and/or the connections of sensor port 219. In some embodiments, the impedance is sensed by providing a relatively small signal of known voltage/current and frequency/frequencies via the electrodes. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 in embodiments also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. In some embodiments, processor 230 is implemented using multiple processor devices, or one or more devices with multiple cores.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

In some embodiments, detection module 232 may also include asystole and bradyarrhythmia detector such as, for example, as disclosed in U.S. patent application Ser. No. 14/029,589, and U.S. patent application Ser. No. 15/614,949.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are sensed or captured according to embodiments, and determining whether a shock criterion is met. The determination can be made from a rhythm analysis of the sensed or captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
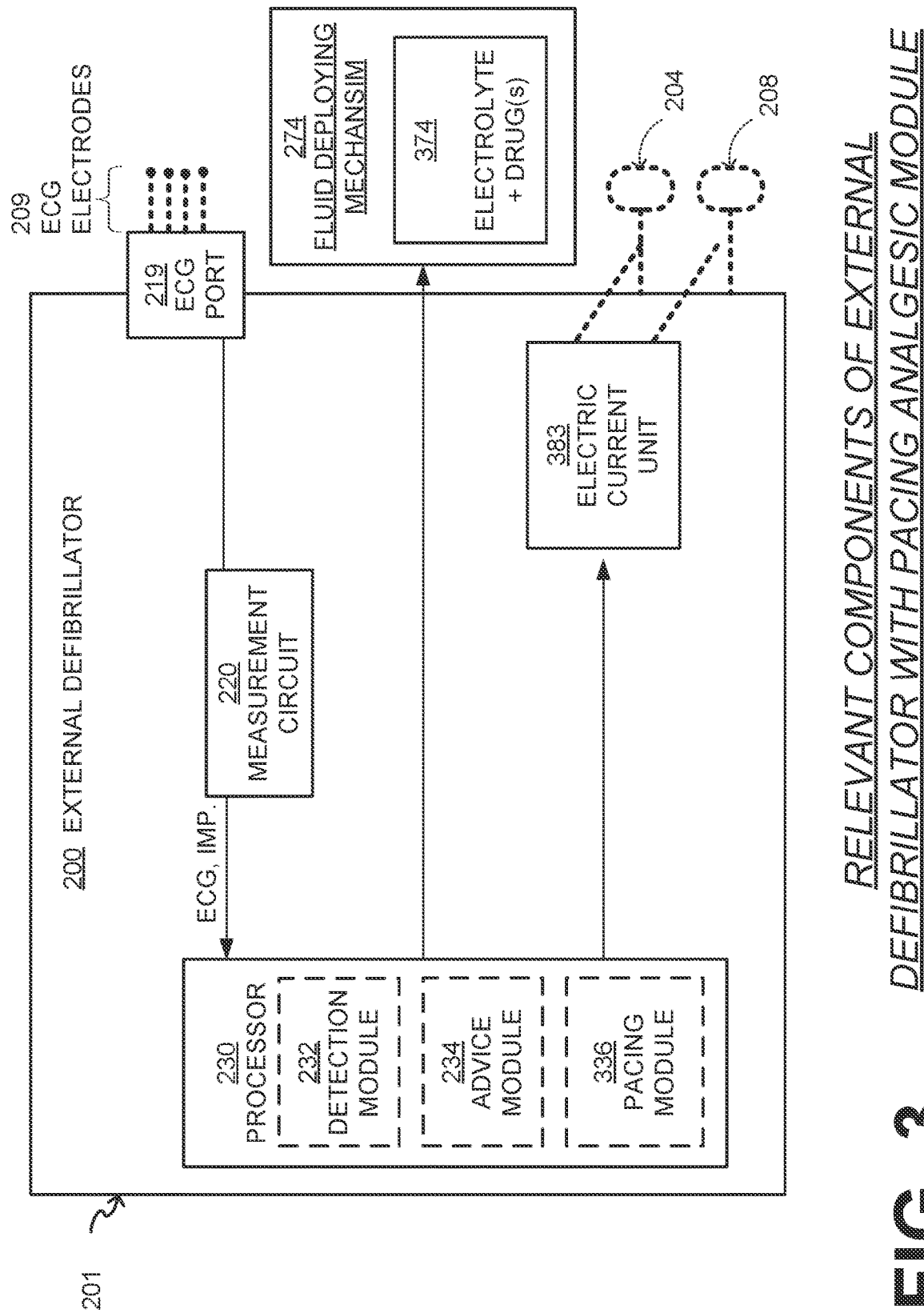
FIG. 3 is a diagram showing sample components of an external defibrillator as in the external defibrillator of FIG. 2, in which some components are shown in more detail, according to embodiments.

FIG. 3 shows sample components of an external defibrillator 200 as in the external defibrillator of FIG. 2, in which some components are shown in more detail, according to embodiments. For the convenience of descriptions, the same elements of the external defibrillator of FIG. 3 and FIG. 2 are marked by the same reference number and will not be described in detail below as they have already been described in detail in conjunction with FIG. 2. That is, when the same reference number appears in different drawings, they refer to the same or like components or steps. In addition, external defibrillator 200 of FIG. 3 also includes other modules and components as shown in FIG. 2, but are omitted in FIG. 3.

WCD patients occasionally experience asystolic death. There are several clinical scenarios that can result in asystole such as, for example: undetected VT/VF, a series of failed shocks, worsening heart failure that causes the heart rate of a supraventricular rhythm to slowly drop, or a sudden complete heart block. For most of these conditions, CPR is likely to be the only effective treatment. However, in some cases transthoracic pacing may benefit such a patient. For example, a patient with complete heart block probably has a viable cardiac pump—it is only lacking a trigger to cause the ventricles to contract. It is possible that transthoracic pacing from a WCD could maintain blood flow for long enough for the patient to receive help (e.g., from EMS).

As previously mentioned, a potential problem in transthoracic pacing in WCD patients is that conscious WCD patients cannot tolerate the pain associated with transthoracic pacing. For example, in one scenario: a WCD patient experiences complete heart block; then the patient loses consciousness; then the patient's heart rate is returned to a normal rate (via transthoracic pacing); then a consciousness is regained by the patient; and then the patient takes measures to stop the pain. If the patient presses the "divert" button on the WCD, the patient would likely experience another cycle of losing and regaining consciousness (repeating the above scenario). If the patient were to remove the WCD support structure or garment to avoid the painful transthoracic pacing therapy, the patient could lose consciousness again, and without the WCD the patient would not receive therapy would probably die.

Further, with standard transthoracic pacing therapy, a WCD patient may not tolerate the therapy well enough to be able to seek help or call EMS. Embodiments described herein can advantageously provide a way to reduce the pain to the point where a patient can tolerate it well enough so that they won't remove the WCD support structure or garment during transthoracic pacing therapy.

Embodiments of external defibrillator 200 (FIG. 3) can advantageously address pain associated with transthoracic pacing. Further, WCD embodiments of external defibrillator 200 can be well suited for transcutaneous delivery of pain-relieving drugs because many WCDs have a mechanism for releasing electrolyte to the patient's skin during or just prior to defibrillation therapy. The electrolyte typically serves as a coupling agent for defibrillation, cardioversion, and/or pacing energy, but as described herein it can also serve to administer medication that may be beneficial.

Figure 3A:
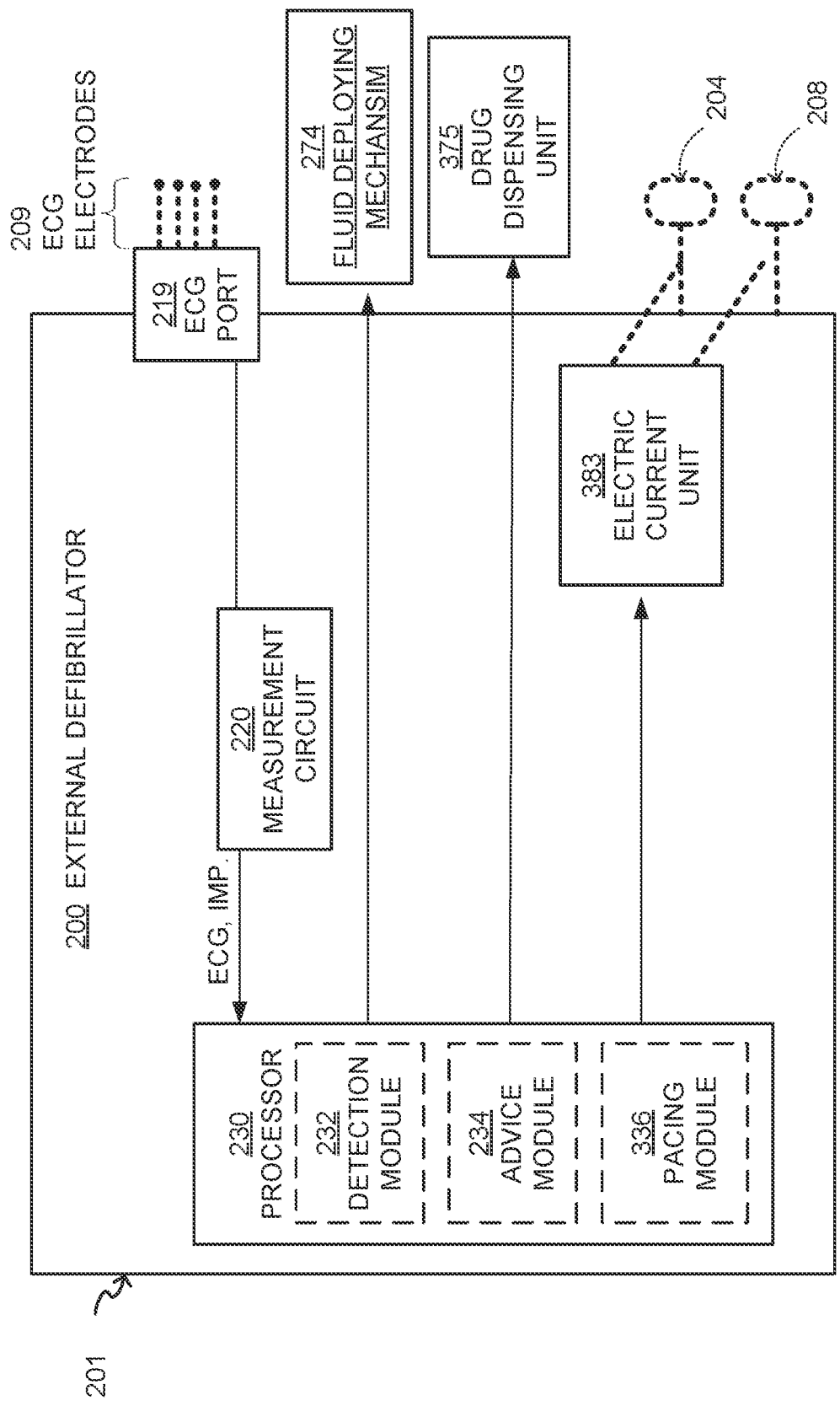
FIG. 3A is a diagram showing sample components of an external defibrillator as in the external defibrillator of FIG. 2, in which some components are shown in more detail, according to other embodiments.

As shown in FIGS. 3 and 3A, embodiments of external defibrillator 200 includes a processor 230 and a fluid deploying mechanism 274. Embodiments of processor 230 and fluid deploying mechanism 274 have been described above in conjunction with FIG. 2. In addition, in some embodiments, processor 230 includes a pacing module 336 and fluid deploying mechanism includes a drug dispensing unit 375 as shown in FIG. 3A. As described further below, fluid deploying mechanism 274 and/or drug dispensing unit 375 include one or more topically-applied drugs to help reduce the pain experienced by a patient receiving pacing therapy. Pacing module 336 is configured to determine whether the patient should receive pacing therapy. In some embodiments, pacing module 336 is implemented, for example, as disclosed in U.S. patent application Ser. No. 14/029,589 and/or U.S. patent application Ser. No. 15/614,949, and can detect bradyarrhythmia and asystole in the patient.

To facilitate absorption of the pain-relieving drug for pacing therapy, some embodiments of external defibrillator 200 are configured to execute a different sequence of preparatory steps for pacing than defibrillation. For defibrillation, no drug absorption is necessary as the patient will be unconscious, so a shock can be delivered as soon as possible after electrolyte release. For pacing, in some embodiments an additional delay is included after the pain-relieving drug is released to allow time for the drug to penetrate the patient's skin.

In some embodiments, pacing module 336 is further configured to provide an alert to the patient prior (for example 5 to 30 seconds prior) to the delivery of the pacing therapy so that pacing therapy will not surprise a conscious patient and allow the patient to divert the pacing therapy. In some embodiments, the alert may also inform the patient that he or she may experience some pain during pacing therapy and/or instruct the patient to not remove the garment.

In some embodiments, the drug dispensing function is implemented using the fluid deploying mechanism 274 that dispenses an electrolyte for defibrillation and cardioversion therapy, with a pain-reducing drug added in the therapy electrode electrolyte or gel as show in FIG. 3. This electrolyte is released onto the patient's skin prior to a shock, either pacing or defibrillation or cardioversion. In some embodiments, the pain-reducing drug included in the electrolyte is an analgesic such as lidocaine to locally "deaden" the skin and surrounding tissue enough to reduce pain during pacing therapy. In some embodiments, the concentration of lidocaine is about 5% solution, which is similar to the concentration in skin patches used for treatment of pain associated with neuralgia. In other embodiments, the concentration of lidocaine in the electrolyte ranges from 0.5% solution to 2%, which can depend on the number of electrolyte reservoirs, the amount of electrolyte dispensed to the patient, the size of the patient, etc. For example, in embodiments in which there are three therapy electrodes/reservoir units used to provide pacing therapy, about 0.033 grams to about 0.166 grams of lidocaine is contained in each electrolyte reservoir. In some embodiments with a different number of electrodes/electrolyte reservoirs used to provide pacing therapy, the concentration of the lidocaine in the electrolyte is set so that the aggregate amount of lidocaine delivered to the patient during pacing therapy is no more than 0.5 grams, and could be less depending on the size of the patient. In other embodiments, different pain-relieving drugs are used in addition to or instead of lidocaine. For example, Marcaine and Articaine are used in some alternative embodiments.

In other embodiments, fluid deploying mechanism 274 includes separate electrolyte reservoirs for defibrillation and pacing (such as, for example, the reservoirs disclosed in the aforementioned U.S. patent application Ser. No. 15/614,949). In some such embodiments, the reservoir(s) for defibrillation therapy do not include pain-relieving drug(s), while the pain-reducing drug(s) are included in the "pacing" reservoir.

In yet other embodiments, drug dispensing unit 375 is separate from the one or more electrolyte reservoirs in fluid deploying mechanism 274 as show in FIG. 3A. Pacing module 336 is configured to trigger the drug dispensing unit 375 to dispense the pain-reducing prior to initiating pacing. In some other embodiments, one or more separate reservoirs are used to hold the drug(s) in the fluid deploying mechanism 274, which processor 230 can cause to dispense the drug(s) either together with or independently of the electrolyte in the reservoirs for defibrillation therapy. Pacing module 336 can be configured to advantageously use these features to dispense the pain relieving drug, wait a set amount of time (e.g., 5 to 30 seconds) to allow it take effect, then cause the electrolyte to be dispensed just prior to the delivery of pacing therapy.

Further, in some embodiments in which pacing module 336 provides an alert to the patient, pacing module 336 can also control drug dispensing unit 375 to dispense the pain-relieving drug(s) a set time after the alert is provided (e.g., to allow the patient to divert the therapy before the drug and/or electrolyte is dispensed), and then wait another set amount of time to allow the pain-relieving drug(s) to take effect before causing the pacing therapy to be delivered. In still other embodiments, the processor 230 is configured to cause the drug dispensing unit 375 to dispense the pain-relieving drug(s) after a successful defibrillation or cardioversion shock (i.e., shocks may injure the patient's skin contacting the therapy electrodes) to reduce any pain experienced by the patient after regaining consciousness.

In some embodiments, fluid deploying mechanism 274 or drug dispensing unit 375 is configured to provide a sedative to the patient. While the pain-reducing drug reduces the pain sensation locally, a sedative has a more systemic effect that reduces the general sensation of pain. The sedative may make the patient drowsy or groggy to the point where they don't care about the pain. In some embodiments, the sedative contains Propofol and is included in the electrolyte at an appropriate or effective dosage so as to provide a light sedation through the patient's skin. Propofol is a fast-acting drug that, unlike many sedatives, has a minimal effect on blood pressure. Propofol patches have been shown to produce a sedative effect in rats, and the administration of electrical pacing pulses may enhance absorption of the drug.

In some embodiments, drug dispensing unit 375 is configured to dispense both a pain-relieving drug and a sedative or drug with systemic effect. The drugs described above are just examples of drugs that might be used. After careful review of the present disclosure, those skilled in the art can implement other embodiments with one or more other drugs that act as a local pain reliever and one or more other drugs that provide a systemic effect.

In some embodiments, processor 230 can selectively control an electric current unit 383 in external defibrillator 200 to provide a relatively small electrical current to the patient. Drug absorption may be increased by the introduction of the small DC electrical current in the range of about 100 µA to about 10 mA. In other embodiments, an AC current is applied. A current flow at this level may be imperceptible to the patient while enhancing drug absorption. In some embodiments, rather than using a separate current unit, electric current unit 383 is implemented using an impedance circuit included in some embodiments of external defibrillator 200 that measures the patient's transthoracic impedance via the therapy electrodes 204 and 208. For example, the impedance circuit provides a small AC current to the patient to measure the patient's transthoracic impedance, and is selectively configurable to also provide the small electrical current used to enhance drug absorption.

In some embodiments, prior to applying pacing pulses to the patient, processor 230 may control drug dispensing unit 375 and electric current circuit 383 to release the electrolyte and prior to initiation of pacing apply a low-level current for a short period of time (ranging from about 5 seconds to 30 seconds, and can range up to 1 minute in some embodiments). This can reduce the pain of the first pacing pulses. The pacing pulses themselves will continue to facilitate drug absorption as the pulses are delivered, but in some embodiments the small drug-infusion current is continued simultaneously with pacing.

In some embodiments, the concentration of each of the one or more drugs in drug dispensing unit 375 are tailored to the patient's needs. For example, a patient with a larger body mass may require a larger dosage to achieve the desired benefit compared to a small patient. In some embodiments, the patient is examined and tested by a doctor or clinician to select what drug or drugs are to be included in the drug dispensing unit 375, the dosage or concentration of the selected drug(s), the timing and/or sequence of the drug delivery (including any delay time for absorption of the selected drug or drugs). In this way it is possible to adjust the dosage for individual patients.

While this disclosure describes the benefits of applying an analgesic and/or a sedative to patients being paced, it is possible that there are other drugs that may benefit WCD patients. For example, Epinephrine (or other drugs that work to increase blood pressure and/or heart rate) may also be dispensed in some embodiments. Epinephrine is often given to cardiac arrest patients to increase their blood pressure post-cardiac arrest. Such WCD embodiments can be advantageously used if it is determined that it is beneficial to increase blood pressure in the patient post-cardiac arrest. In addition, such WCD embodiments can be advantageously used if it is determined that it is beneficial to accelerate the heart rate of a patient experiencing bradycardia. In some embodiments, external defibrillator 200 is configured to control drug dispensing unit 375 to release the electrolyte for the purpose of applying medication, even when external defibrillator 200 is not delivering transthoracic pacing therapy.

In some applications of external defibrillator 200, the doctor or clinician prescribing a WCD for the patient may prefer epinephrine treatment for bradycardia rather than external pacing. In some embodiments, processor 230 is configured to control fluid deploying mechanism 274 (FIG. 3) and/or drug dispensing unit 375 (FIG. 3A) to provide transdermal drug delivery instead of transthoracic pacing in response to detecting a bradycardia. In some embodiments, external defibrillator 200 is configurable to provide either pacing or drug therapy or both, in response to settings inputted or selected by the prescribing doctor or by a technician as instructed by the doctor.

The devices and/or systems mentioned in this document can selectively perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more specialized computers and additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Figure 4:
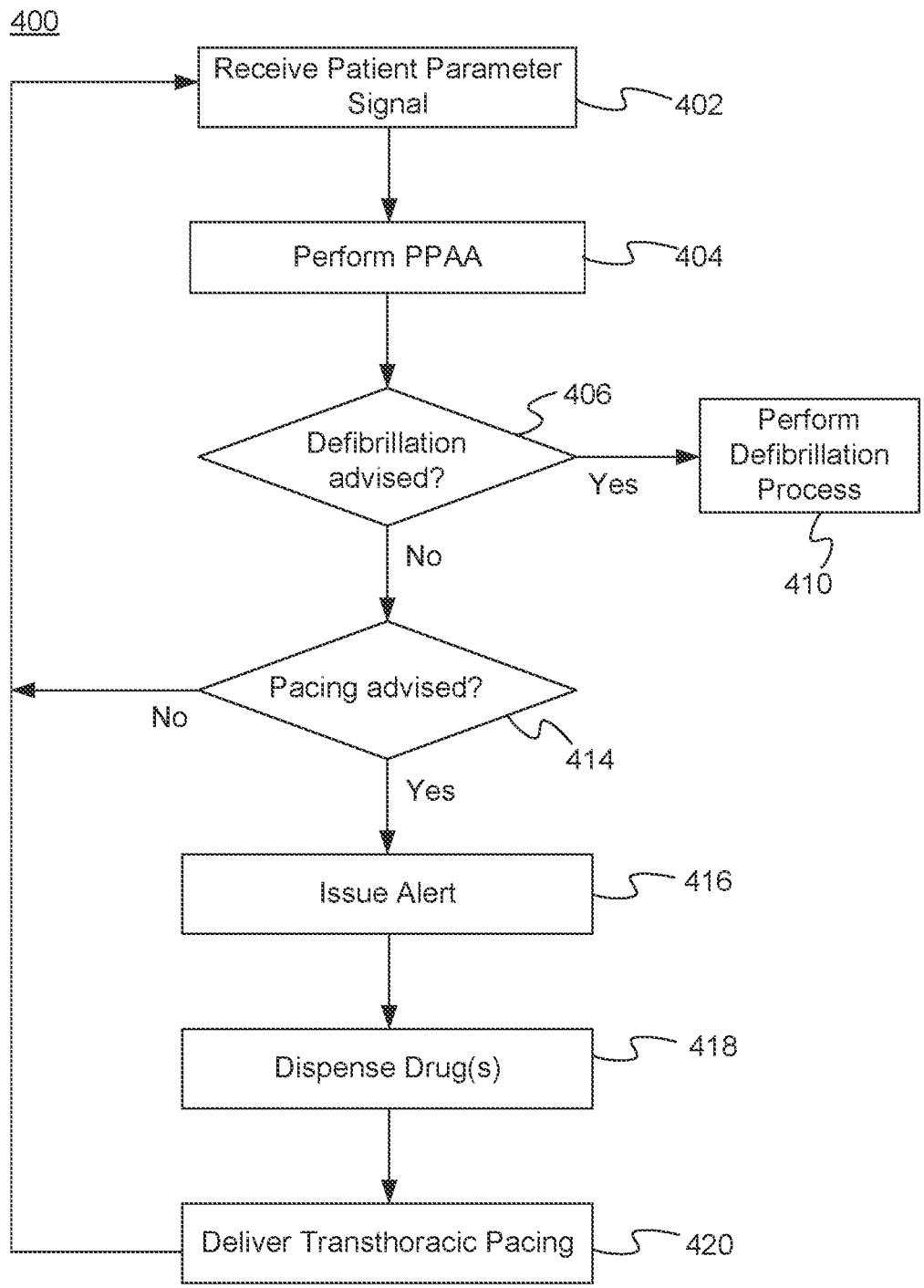
FIG. 4 is a flowchart for illustrating methods of providing one or more drugs to the patient in conjunction with transthoracic therapy according to embodiments.

FIG. 4 show a method 400 for providing one or more drugs to the patient in conjunction with transthoracic therapy by an external defibrillator (e.g., a WCD), according to embodiments. In an operation 402, a patient parameter signal is received. For example, in some embodiments the patient parameter signal is an ECG signal of the patient, but in other embodiments other patient physiological signals are used. In embodiments, the patient's ECG signal is sensed via ECG electrodes and a measurement circuit such as ECG electrodes 209 and measurement circuit 220 described above in conjunction with FIG. 2.

In an operation 404, a patient parameter analysis algorithm (PAAA) is performed. In some embodiments, the PAAA is or comprises a rhythm analysis algorithm (RAA) that is performed or executed on the received ECG signal. In embodiments, the PAAA is performed by a processor of the external defibrillator such as, for example, processor 230 (FIG. 2). In an operation 406, it is determined whether the PAAA advises that the patient should receive defibrillation. In embodiments, this operation is also performed by the processor performing the PAAA. If in operation 406 it is determined defibrillation is advised (e.g., VF is detected), method 400 proceeds to an operation 410 in which the defibrillation process is performed. For example, the defibrillation process may be performed in some embodiments as described in the aforementioned U.S. patent application Ser. Nos. 14/029,589 and/or 15/614,949.

However, if in operation 406 defibrillation is not advised, method 400 proceeds to an operation 414. In operation 414, it is determined whether pacing is advised by the PAAA. In some embodiments, a second type of PAAA or RAAA is performed to determine whether pacing is advised. In embodiments, this operation is performed by the processor performing the PAAA. In some embodiments, the PAAA or the second type of PAAA is configured to advise pacing for complete heart block as well as bradycardia conditions. If in operation 414 it is determined that pacing is not advised, in embodiments method 400 returns to operation 402 to continue monitoring the patient's ECG, or exit method 400 to perform other processes in some other embodiments. However, if it is determined that pacing is advised, in some embodiments method 400 proceeds to an operation 416, while in other embodiments operation 416 is skipped or omitted.

In some embodiments, operation 414 determines whether a drug therapy is advised (rather than pacing), and if so will proceed to operation 416. For example, such embodiments can be advantageously used in WCD in which the prescribing doctor has set the WCD to provide epinephrine drug therapy (instead of pacing) to treat a detected bradycardia.

Further, in some embodiments, operations 406 and 414 are effectively combined in one operation in which the processor in performing the PAAA categorizes the rhythm as one is which defibrillation therapy is advised, pacing therapy is adviced, or no therapy is advised. In other embodiments, the processor categorizes the rhythm for defibrillation therapy, cardioversion therapy, pacing therapy, or no therapy. In still other embodiments, the processor categorizes the rhythm for defibrillation therapy, cardioversion therapy, pacing therapy, drug only therapy, or no therapy.

In operation 416, a pacing alert or warning is provided to the patient. In embodiments, the external defibrillator includes a user interface such as, for example, user interface 280 (FIG. 2) that is controlled by the processor to issue the alert. In some embodiments, the alerts are audio alerts warning or informing the patient that pacing therapy will soon be delivered. In some embodiments, the alert can also or instead include one or more of the following: an instruction or prompt to avoid diverting the pacing therapy; an announcement that a pain relieving drug will soon be delivered, an announcement that a sedative will soon be delivered; an announcement that epinephrine (or other bradycardia drug treatment) will soon be delivered; and/or a prompt to call for assistance (e.g., 911, the patient's doctor, and/or a family member). After review of the present disclosure, one skilled in the art may implement other embodiments of operation 416 with other alerts or prompts.

In an operation 418, one or more drugs are dispensed to the patient in preparation for delivering pacing therapy in accordance with the present disclosure. In embodiments, a drug dispensing unit such as, for example, drug dispensing unit 375 (FIG. 3) is controlled by the processor to dispense the one or more drugs. The drugs can be pain-relievers, sedatives, or others as described above in conjunction with FIG. 3. For example, in some embodiments, lidocaine is dispensed.

In an operation 420, transthoracic pacing is delivered. In some embodiments, the pacing therapy is provided as described in the aforementioned U.S. patent application Ser. Nos. 14/029,589 and/or 15/614,949. In some embodiments in which drug therapy is prescribed instead of pacing therapy for treating bradycardia, operation is 420 is skipped or omitted.

After treatment (which can be pacing or drug therapy as described above), in embodiments method 400 returns to operation 402 to resume monitoring the patient's ECG.

Figure 5:
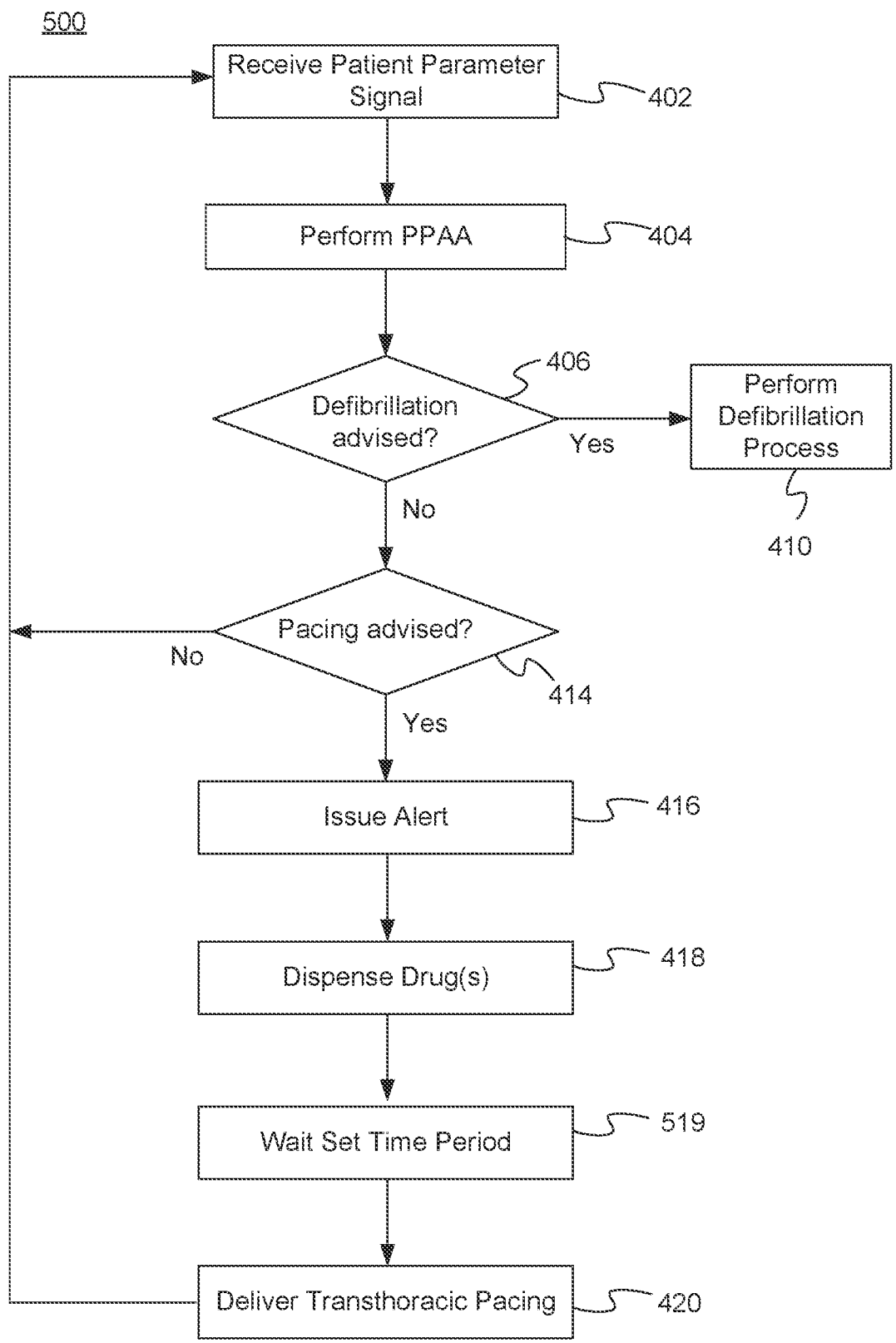
FIG. 5 is a flowchart for illustrating methods of providing one or more drugs to the patient in conjunction with transthoracic therapy according to other embodiments.

FIG. 5 shows a method 500 for providing one or more drugs to the patient in conjunction with transthoracic therapy by an external defibrillator (e.g., a WCD), according to other embodiments. Some embodiments of method 500 include all of the operations of method 400 (FIG. 4), with the addition of an operation to provide some time to allow the dispensed drug to be absorbed by the patient.

In some embodiments of method 500, operations 402, 404, 406, 410, 414, 416, 418 and 420 are performed as described above in conjunction with FIG. 4. However, in embodiments of the method 500, an operation 519 is performed after operation 418 and before operation 420. In operation 519, a predetermined or "set" time period is waited before operation 420 is performed. In embodiments, the processor is configured with the set time period and allows this set time period to elapse from the dispensing of operation 418 before proceeding to operation 420. As previously mentioned, this set time period can advantageously allow the one or more drugs dispensed in operation 418 to be absorbed by the patient. In some embodiments, the set time is set by the prescribing doctor in the external defibrillator based on one or more of the following: the drug or drugs being dispensed, the size of the patient, the gender of the patient, the age of the patient, the health of the patient, the condition detected by the RAA, other medications being taken by the patient, etc. In some embodiments, the set time period can range from about 5 seconds to about 30 seconds.

Figure 6:
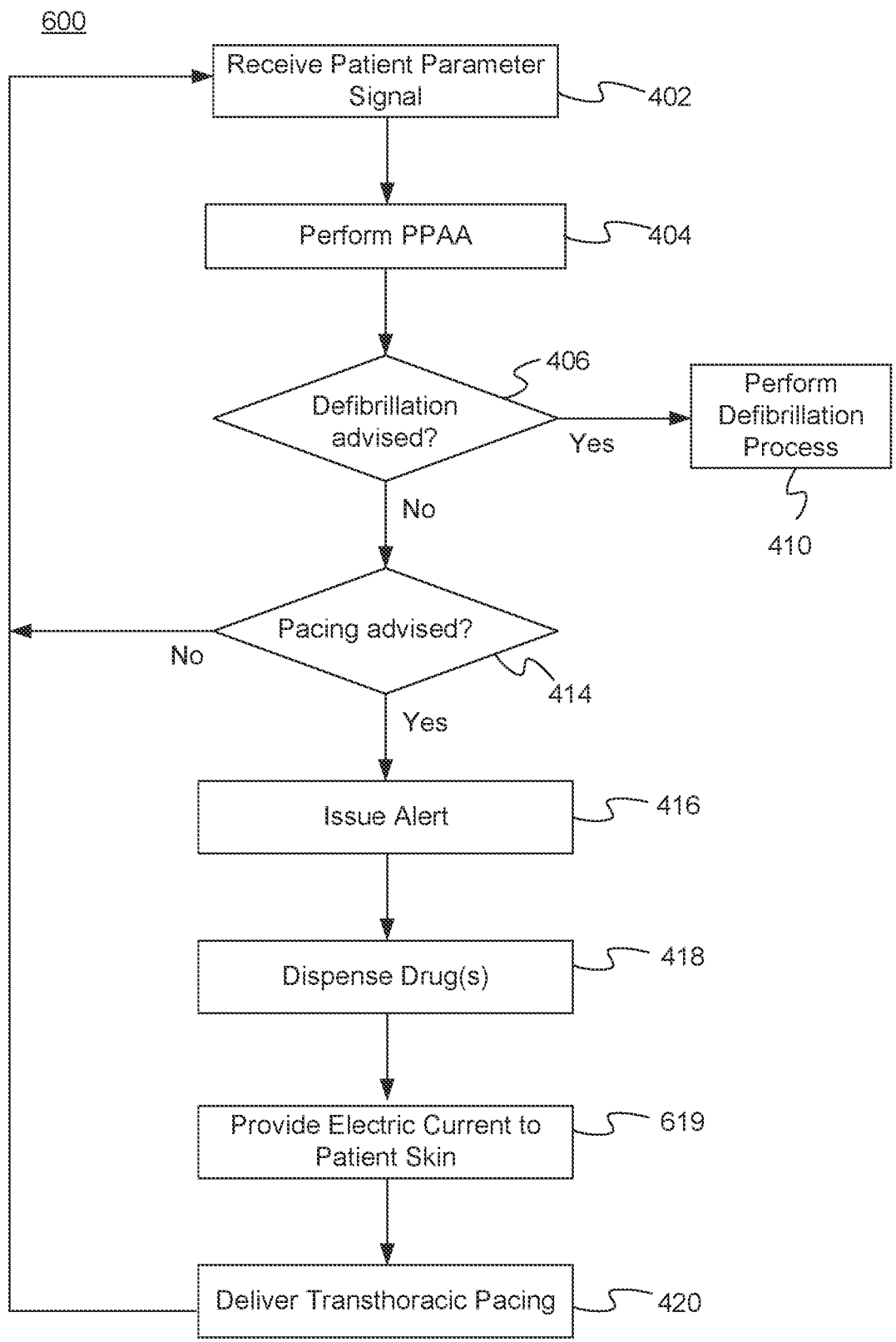
FIG. 6 is a flowchart for illustrating methods of providing one or more drugs to the patient in conjunction with transthoracic therapy according to still other embodiments.

FIG. 6 shows a method 600 for providing one or more drugs to the patient in conjunction with transthoracic therapy by an external defibrillator (e.g., a WCD), according to still other embodiments. Some embodiments of method 600 include all of the operations of method 400 (FIG. 4), with the addition of an operation to provide a relatively small electric current to the patient to assist absorption of the dispensed drug by the patient.

In some embodiments of method 600, operations 402, 404, 406, 410, 414, 416, 418 and 420 are performed as described above in conjunction with FIG. 4. However, in embodiments of the method 600, an operation 619 is performed after operation 418 and before operation 420. In operation 619, a small electric current is applied to patient's skin in the area where the drug is dispensed to enhance absorption of the drug(s) by the patient. In embodiments, an electric current unit such as, for example, electric current unit 383 (FIG. 3) provides the current after the one or more drugs are dispensed. In embodiments, the current is a DC current and ranges from about 100 μA to about 10 mA. In other embodiments, the current is an AC current. In still other embodiments, the current may also be provided while the one or more drugs are being dispensed. In yet other embodiments, operation 519 (FIG. 5) is also performed so that the current provided via operation 619 is flowing during the preset time period provided to allow the dispensed drug(s) to take effect.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator (WCD) system, comprising:
    a support structure configured to be worn by an ambulatory patient;
    an energy storage module configured to store an electrical charge;
    a discharge circuit coupled to the energy storage module;
    a first reservoir in which an electrolyte is contained;
    a second reservoir, distinct from the first reservoir, in which one or more drugs not contained in the first reservoir are contained;
    one or more sensors configured to sense an Electrocardiogram (ECG) signal of the ambulatory patient while the ambulatory patient is wearing the support structure; and
    a processor configured to:
        receive the ECG signal of the ambulatory patient from the one or more sensors,
        perform a first rhythm analysis on the received ECG signal of the ambulatory patient,
        determine whether a shock is advised for the ambulatory patient based on a result of the first rhythm analysis performed on the received ECG signal,
        perform a second rhythm analysis, different from the first rhythm analysis, on the received ECG signal of the ambulatory patient to determine whether pacing therapy is advised for the ambulatory patient,
        in response to a determination that the pacing therapy is advised for the ambulatory patient based on a result of the second rhythm analysis and the shock is not advised based on the result of the first rhythm analysis:
            cause the second reservoir to release the one or more drugs on the ambulatory patient, the one or more drugs comprising a topical sedative, the first reservoir to release the electrolyte on the ambulatory patient, and delay the pacing therapy after a set amount of time has elapsed from the releasing of the one or more drugs and the discharge circuit to discharge the stored electrical charge to deliver the pacing therapy to the ambulatory patient, and in response to a determination that the shock is advised for the ambulatory patient based on the result of the first rhythm analysis;

cause the first reservoir to release the electrolyte and the discharge circuit to discharge the stored electrical charge to deliver the shock to the ambulatory patient, and release the one or more drugs on the ambulatory patient from the second reservoir after the shock is administered, wherein the one or more drugs comprise a topical pain reliever.

2. The WCD system of claim 1, further comprising an electric current unit configured to provide, prior to the delivery of the pacing therapy, an electric current to one or more portions of skin of the ambulatory patient on which the one or more drugs have been released.

3. The WCD system of claim 2, wherein the electric current is delivered to the one or more portions of the skin of the ambulatory patient simultaneously with the pacing therapy.

4. The WCD system of claim 1, wherein the processor is further configured to detect bradycardia and responsive thereto to control the discharge circuit to not deliver the pacing therapy and to cause the one or more drugs formulated to increase blood pressure and/or heart rate of the ambulatory patient to be released on the ambulatory patient.

5. The WCD system of claim 1, wherein the one or more drugs include Propofol.

6. The WCD system of claim 1, wherein the one or more drugs include lidocaine.

7. The WCD system of claim 1, wherein the processor is further configured to determine if the pacing therapy is advised to treat a complete heart block condition based on the result of the second rhythm analysis.

8. A method for use with a wearable cardioverter defibrillator (WCD) system comprising a support structure configured to be worn by an ambulatory patient, a plurality of sensors coupled to or integrated with the support structure configured to sense an Electrocardiogram (ECG) signal of the ambulatory patient, an energy storage module, a discharge circuit, a first reservoir containing an electrolyte, a second reservoir distinct from the first reservoir containing one or more drugs not contained in the first reservoir, and a processor, the method comprising:

receiving the ECG signal from the ambulatory patient using the plurality of sensors;

performing a first rhythm analysis on the received ECG signal from the ambulatory patient;

determining whether a shock is advised for the ambulatory patient based on a result of the first rhythm analysis performed on the received ECG signal;

performing a second rhythm analysis, different from the first rhythm analysis, on the received ECG signal of the ambulatory patient to determine whether pacing therapy is advised for the ambulatory patient;

in response to a determination that the pacing therapy is advised for the ambulatory patient based on a result of the second rhythm analysis and the shock is not advised based on the result of the first rhythm analysis;

causing, by the processor, the second reservoir to release the one or more drugs on the ambulatory patient, the one or more drugs comprising a topical sedative, causing, by the processor, the first reservoir to release the electrolyte on the ambulatory patient, delaying, by the processor, the pacing therapy after a set amount of time has elapsed from the releasing of the one or more drugs, and controlling, by the processor, the discharge circuit to discharge the stored electrical charge to deliver the pacing therapy to the ambulatory patient; and in response to a determination that the shock is advised for the ambulatory patient based on the result of the first rhythm analysis;

causing the first reservoir to release an electrolyte and controlling, by the processor, the discharge circuit to discharge the stored electrical charge to deliver the shock to the ambulatory patient, and releasing the one or more drugs from the second reservoir on the ambulatory patient after the shock is administered, wherein the one or more drugs comprise a topical pain reliever.

9. The method of claim 8, further comprising providing, prior to the delivery of the pacing therapy, an electric current to one or more portions of skin of the ambulatory patient on which the one or more drugs have been released.

10. The method of claim 9, further comprising delivering the electric current to the one or more portions of the skin of the ambulatory patient simultaneously with the pacing therapy.

11. The method of claim 8, further comprising determining, from the received ECG signal, that the patient is experiencing bradycardia and responsive thereto controlling the discharge circuit to not deliver the pacing therapy and to cause the one or more drugs formulated to increase blood pressure and/or heart rate of the ambulatory patient to be released on the ambulatory patient.

12. The method of claim 8, wherein the one or more drugs include Propofol.

13. The method of claim 8, wherein determining whether the pacing therapy is advised comprises determining whether the ambulatory patient has a complete heart block condition based on the result of the second rhythm analysis.

14. The method of claim 8, wherein the one or more drugs include lidocaine.

15. An electrode system for use with an external defibrillator and external pacing device, the electrode system comprising:

an electrolyte reservoir configured to release an electrolyte;

at least one electrode configured to:

conduct a shock to a patient, based on a first rhythm analysis performed on an Electrocardiogram (ECG) signal of the patient, after the electrolyte is released between a surface of the at least one electrode and a skin of the patient, wherein the shock is delivered after a set time period has elapsed from releasing the electrolyte, and conduct pacing pulses to the patient based on a second rhythm analysis, different from the first rhythm analysis, performed on the ECG signal of the patient; and a drug dispensing unit that is distinct from the electrolyte reservoir configured to topically release one or more drugs that are not contained in the electrolyte reservoir after the pacing is conducted, wherein the one or more drugs comprise a topical sedative, and wherein the drug dispensing unit is a second reservoir.

16. The electrode system of claim 15, wherein the drug dispensing unit is configured to release the one or more drugs alternately with the electrolyte that is subsequently released after a set amount of time after the one or more drugs are released between a surface of the at least one electrode and a portion of the skin of the patient such that the one or more drugs contact the portion of the skin to penetrate into the skin and the electrolyte contacts the surface of the at least one electrode.

17. The electrode system of claim 15, wherein the one or more drugs further comprise a topical pain reliever and/or a drug formulated to increase the blood pressure and/or heart rate of the patient.

18. The electrode system of claim 15, further comprising an electric current unit configured to provide an electric current to the portion of the skin of the patient via the at least one electrode.

19. The electrode system of claim 18, wherein the electric current is the shock when the electrolyte reservoir releases the electrolyte, and wherein the electric current is a pacing pulse when the drug dispensing unit releases the one or more drugs.

20. The electrode system of claim 18, wherein the electric current is configured to be applied to the portion of the skin of the patient while the patient is receiving the pacing.

* * * * *